United States Patent [19]

Branco

[11] Patent Number: 4,974,592
[45] Date of Patent: Dec. 4, 1990

[54] CONTINUOUS ON-LINE BLOOD MONITORING SYSTEM

[75] Inventor: Flavio S. C. Branco, Northridge, Calif.

[73] Assignee: American Sensor Systems Corporation, Montebello, Calif.

[21] Appl. No.: 270,960

[22] Filed: Nov. 14, 1988

[51] Int. Cl.$^5$ .............................................. A61B 5/00
[52] U.S. Cl. .................................. 128/635; 204/403; 204/409; 204/411; 204/416
[58] Field of Search ................ 128/635; 204/403, 409, 204/411, 416

[56] References Cited

U.S. PATENT DOCUMENTS

| | | |
|---|---|---|
| 4,020,830 | 5/1977 | Johnson et al. . |
| 4,130,227 | 7/1978 | Zemel . |
| 4,172,770 | 10/1979 | Semersky et al. . |
| 4,180,771 | 12/1979 | Guckel . |
| 4,218,298 | 8/1980 | Shimada et al. . |
| 4,238,757 | 12/1980 | Schenck . |
| 4,267,504 | 5/1981 | Bergveld . |
| 4,269,682 | 5/1981 | Yano et al. . |
| 4,280,889 | 7/1981 | Szonntagh . |
| 4,314,824 | 2/1982 | Hansen et al. . |
| 4,315,754 | 2/1982 | Ruzicka et al. . |
| 4,322,680 | 3/1982 | Janata et al. . |
| 4,352,726 | 10/1982 | Sugano et al. . |
| 4,397,714 | 8/1983 | Janata et al. . |
| 4,399,225 | 8/1983 | Hansen et al. . |
| 4,411,741 | 10/1983 | Janata . |
| 4,488,556 | 12/1984 | Ho . |
| 4,502,938 | 3/1985 | Covington et al. . |
| 4,508,613 | 4/1985 | Busta et al. . |
| 4,514,263 | 4/1985 | Janata . |
| 4,534,825 | 8/1985 | Konig et al. . |
| 4,589,970 | 5/1986 | Ligtenberg et al. . |
| 4,636,827 | 1/1987 | Rudolf . |
| 4,641,249 | 2/1987 | Gion et al. . |
| 4,657,658 | 4/1987 | Sibbald . |
| 4,734,184 | 3/1988 | Burleigh et al. ................ 128/635 X |
| 4,786,394 | 11/1988 | Enzer et al. ..................... 128/635 X |

FOREIGN PATENT DOCUMENTS

86/05590 · 9/1986 PCT Int'l Appl. .

OTHER PUBLICATIONS

Sibbald, A., Covington, A. K. and Cooper, E. A., "On--Line Measurement of Potassium in Blood by Chemical-Sensitive Field-Effect Transistors: A Preliminary Report." 29, *Clin. Chem.*, 405–406 (1983).

Sibbald, A. and Covington, A. K., "Online Patent-Monitoring System for the Simultaneous Analysis of Blood $K^t$, $Ca^{2t}$, $Na^t$ and pH Using a Quadruple-Function ChemFET Integrated-Circuit Sensor." *Medical & Biological Engineering & Computing*, 23, pp. 329–338 (1985).

"Tomorrow in Brief." The Futurist, p. 3, May–Jun., 1987.

*Primary Examiner*—Lee S. Cohen
*Attorney, Agent, or Firm*—Lyon & Lyon

[57] ABSTRACT

A continuous on-line blood monitoring system for determining the ionic concentrations of certain ions within blood is disclosed. By use of a synchronized valving mechanism within the device, as well as locating the amplification electronics away from the sensor elements, a relatively small, but highly efficient analyzing system is provided.

11 Claims, 5 Drawing Sheets

CONTINUOUS ON-LINE BLOOD MONITORING SYSTEM

FIELD OF THE INVENTION

The invention relates generally to a system for monitoring blood, and more specifically to a system for continuous, on-line monitoring of the specific ionic concentration of any of several ionic components of blood.

BACKGROUND OF THE INVENTION

Description of Related Art

Publications and other materials used to illuminate the Background, Summary and Detailed Description of the Invention are incorporated herein by reference.

The application of this invention is directed primarily to the life threatening situations encountered in the trauma centers and operating rooms, where prompt action is essential. Current practices of performing blood analysis in the laboratory or in equipment which require from one quarter of an hour or more to provide results is in many cases inadequate and the patient's life is placed in jeopardy due to this delay.

To facilitate the analysis of the blood of an individual, and specifically the ionic concentration of several ionic components of the blood, the system described herein accomplishes this task in a superior manner over similar prior art devices. The analysis of the ionic concentration in blood require special sensors which can respond selectively to the particular ion of which the concentration is being measured.

As the skilled artisan will readily appreciate, the ionic concentration within blood plays a dominant role in the health of an individual, and therefore, fluctuations in the ionic concentration of certain ionic compounds can have serious implications for the individual. For example, in patients with arrhythmias, cardiac shock, and myocardial infarctions, such ionic concentrations may change substantially over the course of treatment of a patient, and the measurement of such change in ionic concentration can provide critical information with respect to the well being of the patient. Ionic concentrations may also change during the course of surgery, during pharmacological therapy, the administration of fluid and electrolytes to the patient, and during other types of medical treatments and procedures. In all of the above scenarios, the measurement and monitoring of ionic concentration levels may be, and, in fact, usually is, required on a fairly continuous basis. This of course can create additional problems for the patient in that relatively large quantities of blood must be continually removed and analyzed, and such continuous removal can create patient discomfort, and, depending on the nature of the condition of the patient, may be impossible.

In order to achieve a "real time" analysis of the various concentrations of ions within a patients blood, and hence obtain more accurate values for course-of-treatment determinations, the amount of time between when the blood to be analyzed ("analyte") leaves the patient and is analyzed must be minimal. Additionally, the temperature of the analyte should be as close to the temperature of the patient's blood as possible. Finally, in order to limit exsanguination, a system designed for continuous monitoring of ionic concentration for extended periods of time requires the removal of as little blood as possible from the patient.

The current state of the art utilizes selective membranes applied directly to the gate of a field effect transistor in order to analyze the ionic concentration in blood. Such transistors with a selective membrane so applied are known as "ChemFETS." For example, in U.S. Pat. No. 4,180,771, a semiconducting substrate is described having a gate insulator of an electrically insulatory material overlapping a portion of a substrate other than that covered by a gate insulator, such that when the chemically sensitive layer is exposed to a solution, the electric field in the substrate is modified, which changes the conductance of the channel between a source region and drain region. This change in conductance is related to chemical exposure and can be directed with a measuring device, e.g., a current meter. A similar device is also described in U.S. Pat. No. 4,322,680. Reference is also made to U.S. Pat. No. 4,448,556.

In U.S. Pat. No. 4,641,249, there is described a device which compensates for temperature-dependent characteristic changes in ion-sensitive field-effect transistors. Sibbald, Covington and Carter, in "Online patient-monitoring system for the simultaneous analysis of blood $K^+$, $Ca^{2+}$, $Na^+$ and pH using a quadruple-function ChemFET integrated-circuit sensor" *Med & Bio. Eng. & Comp.* 23:329-338 (1985) (hereinafter "Sibbald"), describe a continuous on-line system for analyzing blood $K^+$, $Ca^{2+}$, $Na^+$ and pH whereby a ChemFET device is incorporated into a miniature flow through cell. The system uses a small analyte sample (30 ul). The system also utilizes a pinch-tube sampling valve, a heat exchanger and a reference electrode. An analyte-chopping analysis (ACA) system is also utilized in which analyte samples are sent to the ChemFET in alternation with a calibration solution which is chosen to provide baseline ion concentration levels such that each calibration solution acts as a reference datum for the evaluation of the data from the analyte samples. A microcomputer controls the alternating flow of blood and baseline solution through the ChemFET See also, Sibbald, Covington & Cooper, "On-Line Measurement of Potassium in Blood by Chemical-Sensitive Field Effect Transistor: A Preliminary Report" *Clin. Chem* 29:405-06 (1983) and U.S. Pat. No. 4,502,938. The system is not, however, without serious problems relative to the objective of the system, i.e., an accurate, real-time analysis of the ionic concentration levels of an individual's blood.

As noted in Sibbald, supra, ChemFET devices exhibit some thermal sensitivity. Thus, fluctuation in analyte temperature (caused by the difference in temperature between the baseline solution at ambient and blood at body temperature) can interfere with the sensitive analysis of the ChemFET. Additionally, and not discussed in Sibbald, is that the use of a 12V solenoid valve for closing the tubing lines inherently generates heat within close proximity to the ChemFET. In order to compensate for the problems of "heat," Sibbald describes the use of a small glass heat exchanger, whereby blood passes down a narrow central portion of the exchanger, which is surrounded by a relatively large volume of baseline solution. Thus, and as is also noted in Sibbald, the outflow of baseline solution must be much greater than that of the warm analyte (a 3 to 1 ratio is disclosed) to effectuate adequate heat exchange efficiency. The need for this type of arrangement not only generates severe restrictions on the design of the system, but also the utility and effectiveness of the system. It is also recognized in Sibbald that it is preferable to analyze the blood at body temperature, which, in accordance with the Sibbald system, is difficult. Additionally, Sibbald adds that monitoring more than four ionic species simultaneously creates considerable engineering difficulties. It is to these problems that the present invention is directed.

None of the prior art devices effectuates the objective of the present invention, i.e., utilization of less then 8 microliters of blood in the analyte chamber, with an overall total volume of analyte in transit of less then 20 microliters; an analysis cycle of less than one minute; a low cost, disposable sensor capable of analyzing efficiently numerous blood component concentrations; a piston actuator valve system devoid of electrically operated mechanisms; low cost, disposable tubing for the analyte; and, most importantly, a truly continuous on-line monitoring system whereby the patient's exsanguination is less then 20 cc/24 hours. Thus, the present invention allows for the precise measurement of the analyte ionic concentration over a continuous period of time, such that a proper analysis of discrete and drastic fluctuations can be made. In this way, critical data is continually provided to those responsible for the care of the patient.

SUMMARY OF THE INVENTION

Accordingly, the present invention provides for the continuous analysis of the ionic concentration in blood such that both the flow of blood from the patient to the analyzer is as minimal as possible, and the lag time between the time the blood leaves the patient and the time at which the analysis is made is as minimal as possible.

The sensors utilized in accordance with the present invention are of an extremely small design. Such sensors must of course also be very accurate and reliable. Finally, such sensors, because they come into direct contact with the patient's blood, are disposable. These criteria are satisfied by having the sensors become "passive" such that they contain only an electrode, covered by an ion selective membrane and the reference electrode. In accordance with the present invention, the burden of amplification of the signal generated by the sensor is removed from the sensor area. As the skilled artisan will readily appreciate, by keeping the sensors separate from the amplification/measuring instrumentation, the constraints which are fundamentally a part of the prior art devices that do not separate the amplification means from the sensor, are automatically negated. As such, the measuring instrumentation can be designed to vastly improve the job of amplification of the very weak signals generated from the ionic concentration at the site of the membrane as determined by the sensors, because the constraints of size and temperature problems are more readily dealt with when such instrumentation is located away from the sensors. Additionally, because the sensor design of the present invention is "passive," i.e., it does not contain electronic amplification and therefore is less complicated than the prior art ChemFET sensors, the sensors of the present invention have an appreciable lower production cost.

In accordance with another aspect of the present invention, low analyte consumption is satisfied by means for controlling the flow of both the analyte and standard solution This method allows for the passage of the standard solution and analyte over the sensors in a seriatim manner such that when the standard flows across the sensor in order to generate a baseline reading, the analyte does not flow across the sensor; when the analyte flows across the sensor, the standard solution does not. The method allows the analyte to be submitted to the sensors alternating with a standard solution which serves as a baseline to calibrate the measuring instrumentation prior to the submission of every analyte sample as well as to "flush" the system prior to each sampling cycle. It is necessary, therefore, to have the standard solution and the analyte flow through tubing which leads to the sensors without mixing. Mixing can occur in the zone which separates the baseline solution from the analyte; in this area some diffusion of one fluid into another is inevitable. However, in other zones of the line, the alteration of baseline and analyte prevents such diffusion.

In order to accomplish this task, it is necessary to utilize special valves which are synchronized to open the baseline feed-line while maintaining the analyte feed-line closed, then opening the feed-line while keeping the analyte feed-line closed. Valves operating under open-close conditions have heretofore been utilized in prior ionic concentration measuring devices, as in: Sibbald, supra; Sibbald et al., U.S. Pat. No. 4,657,658; Hansen et al., U.S. Pat. No. 4,399,225; Ruzicka et al., U.S. Pat. No. 4,315,754; Hensen et al., U.S. Pat. No. 4,314,824; Janata et al., U.S. Pat. No. 4,322,680. These actions are typically accomplished by utilization of valves actuated by electrical energy. Additionally, such valves are typically located in the immediate proximity of the sensor. Because of this, the inherent "bulkiness" of such valves, their weight, the heat generated from their operation, as well as the power which they consume make these types of valves less than ideal to perform the required function. Discrete fluctuations in analyte temperature, which necessarily impacts upon the accuracy of the measurement, are not avoidable by having an electrically operated valve in the vicinity of the sensor, yet continual baseline—blood measurements must occur in order to obtain a proper measurement of ionic concentration. Thus, by utilizing a sensor system separate from the amplification and measuring instrumentation, non-electrical, smaller, light-weight valves can be utilized which accomplish this necessary task in a superior and efficient manner over the prior art.

The valves utilized in accordance with the present invention are of a piston-type design, whereby a fluid (either air or liquid) occupies the interior portion of both the tubing connected to the piston/cylinder actuator area as well as the piston/cylinder actuator housing area. Operatively connected to the fluid line is a fluid-pump mechanism, which, when activated, can increase the pressure upon the fluid within the line. As is readily appreciated, an increase in pressure upon the fluid will cause the fluid to flow into the fluid-pump mechanism, thus causing the fluid therein to exert an outwardly moving force upon the actuator. When this happens, a piston connected to said piston-pump is forced outwardly, and with sufficient pressure, the piston engaging either the analyte or baseline tubing will effectively prevent the flow of either analyte or baseline solution. Alternatively, a "Bowden" type cable can be utilized to operate the actuator.

Several advantages are occasioned by the use of such a mechanism. First, and foremost, the removal of an electrically operated valving mechanism negates additional excess heat within the systems. As such, by utilization of such a mechanism, a ChemFET device could be utilized in the present invention as an alternative to the use of the analyzing device of the present invention. Secondly, a mechanism operated by fluid pressure, as opposed to electrical energy, is less likely to succumb to the normal degradation and failures seen in electrical devices. Finally, if a homogeneous temperature is required within the analyzing area, the temperature of the fluid can be monitored and stabilized to maintain such homogeneity.

In order to accomplish the goal of providing a truly efficient, continuous on-line monitoring system, the active areas of the sensor required to produce usable sensitivity will be very small to allow for a small sensor chamber volume such that the volume of analyte required is advantageously minimal. By accomplishing this goal, only a minimal amount of blood must be removed from the patient, while not compromising on the absolute and critical need for accurate analysis.

The following drawings are set forth for illustrative purposes and are not to be construed as limiting or constricting the claims of the present invention in any manner. Additionally, for purposes of simplicity, the drawings depict a design utilizing five sensors corresponding to measurement of five ions. However, it is understood that the number of sensors that can be utilized in the present invention is not to be limited merely by the illustrations herein.

DESCRIPTION OF THE PREFERRED EMBODIMENT

Figure 1:
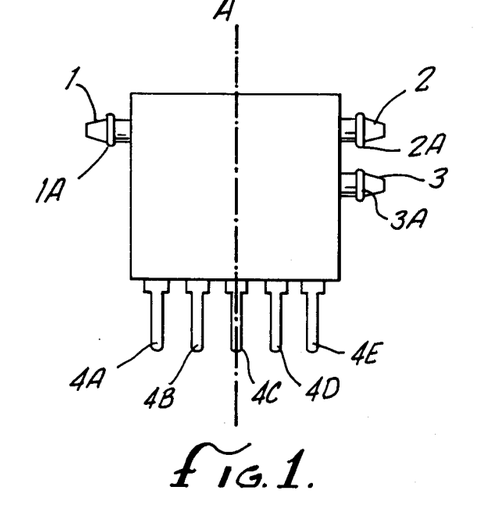
FIG. 1 illustrates the disposable biochemical sensor in accordance with the present invention.

Housing 10 provides for a single input connection 1 for the analyte, one input connection 3 for the reference solution, and one output connection 2 for the waste fluids. Sensor output terminals 4A, 4B, 4C, 4D and 4E are molded into the half 10a of sensor housing 10. These terminals are disposed in a linear pattern which matches that of a miniature connector 224 associated with the hybrid circuit shown in FIG. 5 as part 220. This connector provides for easy installation and removal of the sensors after use. Additionally, analyte input connections 1 and 3 are designed to have lips 1A and 3A, respectively, which allows for a tight and secure connection. In the same manner, waste output 2 also provides for a similar lip 2A.

Figure 2:
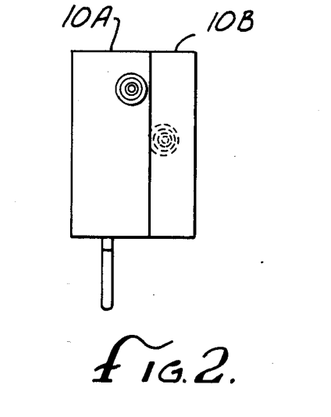
FIG. 2 is a side view of FIG. 1.
Figure 3:
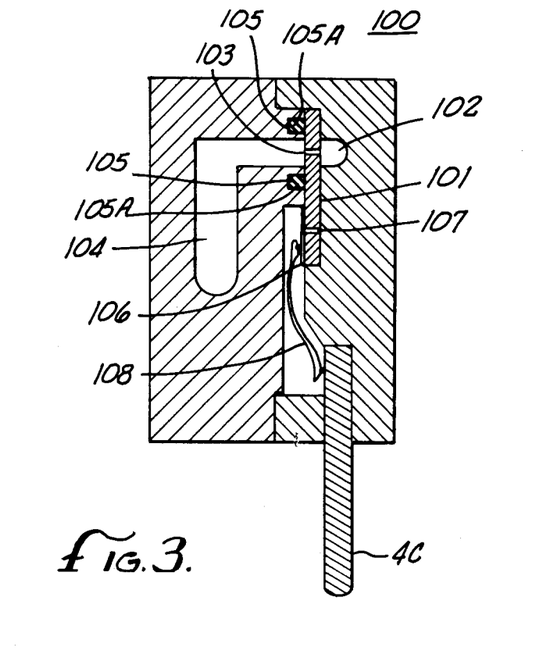
FIG. 3 is a cross section through line A—A of the sensor of FIG. 1.

As illustrated in FIG. 2, housing 10 is fabricated into two halves 10A and 10B to allow for assembly of sensor 100, which is depicted in detail in FIG. 3. Sensor plate 101 (FIG. 4) is installed and set in place with an inert and stable bonding epoxy type cement or other such material which seals completely plate 101 against the periphery of analyte channel 102. Plate 101 has its sensors exposed to one wall of channel 102. Additionally, the ends of channel 102 are connected respectively to analyte input 1 and waste output 2 in such a way that when the analyte flows through channel 102, the analyte comes in contact with each sensor element of the sensor plate.

Figure 4A:
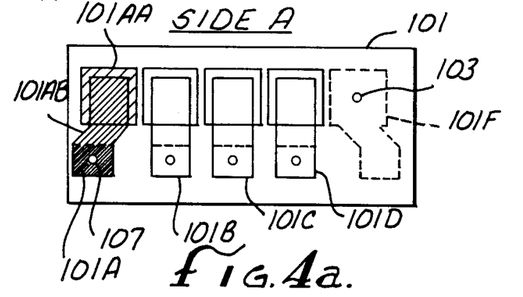
FIGS. 4a and 4b are detailed illustrations of the sensor plate of FIG. 1.
Figure 4B:
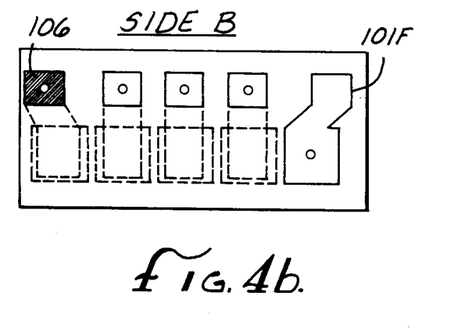

Downstream from the sensor elements 101A-D, sensor plate 101 has a very small perforation 103, the diameter of which is on the order of a few thousand microns. Perforation 103 is produced by a laser-beam method and allows for ionic contact with the reference solution which is fed at a very low rate from the reference channel 104 on the opposite side of plate 101. The pressure of the reference solution in channel 104 is adjusted so as to allow for a flow of reference solution of just a few microliters per hour, which avoids clogging of perforation 103, which is in the order of between 500 and 2000 microns in diameter, preferably 1000 microns in diameter.

Opposite to sensor elements 101A-D and exposed to channel 104, plate 101 has a metallic pattern established by vapor deposition methods or screening or any other suitable method. This metallic pattern can be of any of the noble metals such as silver, gold, platinum or palladium. The reference pattern and metallic patterns of elements 101A-D extend away from the area of contact with the reference and analyte solutions, respectively, and are overlaid with silver/palladium pads 106 for easy wirebonding to output terminals 4A, 4B, 4C, 4D and 4E.

Channel 104 is sealed by an elastic sealing "O" ring 105 made of rubber, neoprene or any other suitable material. This ring seats in a nest 105A in the top of housing 10A and presses against the glass substrate of plate 101, providing a tight seal for the reference solution.

The connections of elements 101A-D to pads 106 is done via plated-thru holes, e.g., 107 (having the same diameter range of perforation 103), a conventional technique used in hybrid circuits and printed wiring boards.

Sensor plate 101 is fabricated of glass, quartz or any glasslike material of low porosity, great mechanical stability, inert to the analyte and reference solutions, and capable of withstanding without deformation the elevated temperatures required during the fabrication process, such as the baking of the pads 106. One side of plate 101 receives a series of metallic patterns 101A, each pattern corresponding to each sensor element. The metal used must not react with the analyte or the reference solution. The thickness of the pattern may be from several microns to several thousand microns. As is readily seen, the metallic pattern form the sensor electrodes 101A-D.

Sensor electrodes 101A-D consist of an active area (i.e. 101AA) over which an ion selective membrane is applied and an extended area (i.e. 101AB) which serves the purpose of connecting the active area to e.g., the sensor terminal 4A. The active area of electrodes 101A-D is approximately two square millimeters. However, the latitude of this parameter is relatively, but very, large. For example, an area one hundred times smaller would be sufficient to yield satisfactory results. Part of the extended area is overlaid with a thin layer of silver/palladium to allow for binding wire 108 which connect electrodes 101A-D to the respective output terminals, e.g. 4A.

The selective membrane is formulated to provide the required selectivity to the desired ion. The method of application of the membrane must yield both uniform and repeatable characteristics. This can be accomplished by evaporation of a measured amount of a fixed concentration of the membrane compound applied over the electrode's active area. This area of the membrane must be slightly longer than the area of the active electrode so that it completely overlaps it. On the opposite side of electrodes 101A-D is deposited a reference electrode 101F similar to the sensor electrodes. Electrode 101F is located downstream from electrodes 101A-D and may be made from any of the noble metals.

Figure 5:
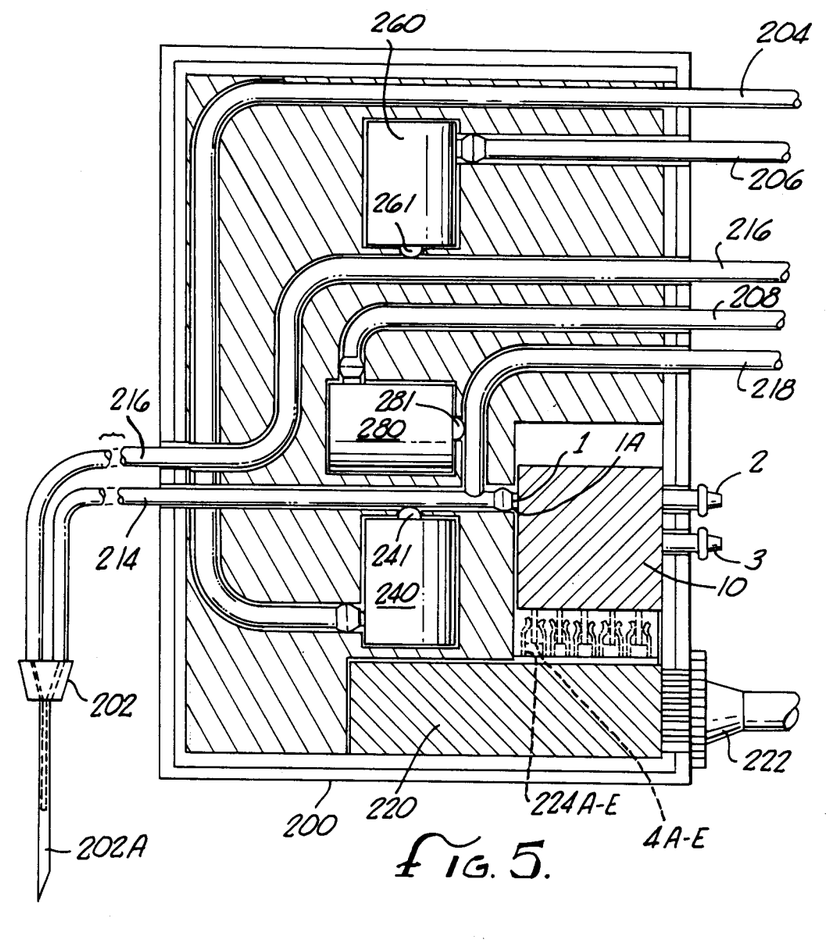
FIG. 5 is a detailed illustration of the internal portion of the sensor housing assembly.

As illustrated in FIG. 5, the entire internal view of the housing assembly 200 is set forth. Sensor housing 10 is shown with analyte input 1 snugly connected to analyte tube 214 by means of input lip 1A. Tube 214 (which allows for the delivery of blood from the patient, mixed with heparin, to housing 10) is receivably connected to dual lumen canula 202, the end 202A of which is inserted into the vein of the patient. Canula 202 also is receivably connected to tubing 216 which provides for the introduction of heparin to the canula. Tube 218 allows for introduction of baseline solution into sensor housing 10. Additionally, canula 202 is disposable.

Because an important feature of the present invention is to provide for the switching of the flow of both analyte and baseline solution to sensor 10, tubing 218 and 214 (as well as 216) is made of an elastic material. Thus, for the purposes of this invention, "elastic" means that which can be pinched closed by the valve mechanism of the present invention, such that the flow of solution through the tubing is sufficiently prevented during operating of the valve mechanism. Tubing 218, 216 and 214 have an outside diameter of approximately two millimeters and an internal diameter of approximately one half millimeter. As illustrated in FIG. 5, piston/cylinder actuator 240 is located adjacent tubing 214 with piston 241 in connection therewith; piston/cylinder actuator 280 is located adjacent tubing 218 with piston 281 in connection therewith; and piston/cylinder actuator 260 is located adjacent tubing 216 with piston 261 in connection therewith. Control of such actuators is effectuated by fluid pressure on the pistons whereby fluid is maintained in tubing 204, 206 and 208, respectively. Tubing 204, 206 and 208 are in turn connected to a fluid pump (not shown) which is in turn controlled by a computer (not shown). Thus when the pressure in tubing 204, 206 and 208 increases, pistons 241, 261 and 281, respectively, move in contact with and pinch-off tubing 214, 216 and 218, respectively.

Figure 6:
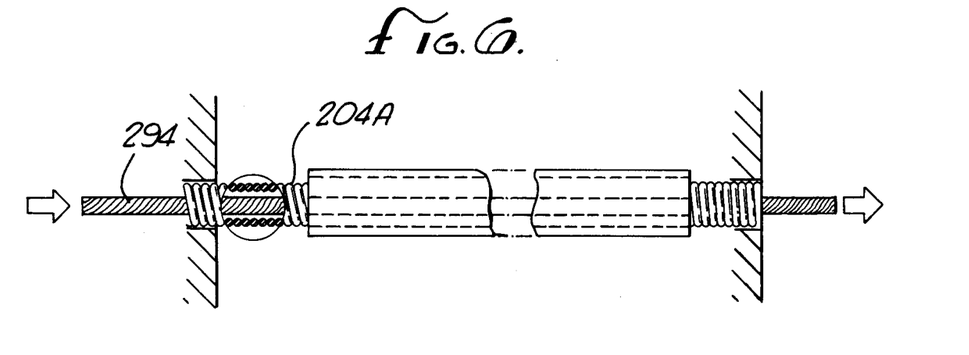
FIG. 6 is an alternative embodiment of another method for use in activating a piston/cylinder actuator.

The operation of the piston/valve actuators 240, 260 or 280 may alternatively be accomplished by mechanical actuation using "Bowden" cables, as illustrated in FIG. 6. Thus, for example, tubing 204A contains flexible, very small diameter twisted steel cables 294. Cables 294, being somewhat more rigid than fluid, can transmit force and displacement to, e.g. piston 261 (FIG. 5).

Figure 7:
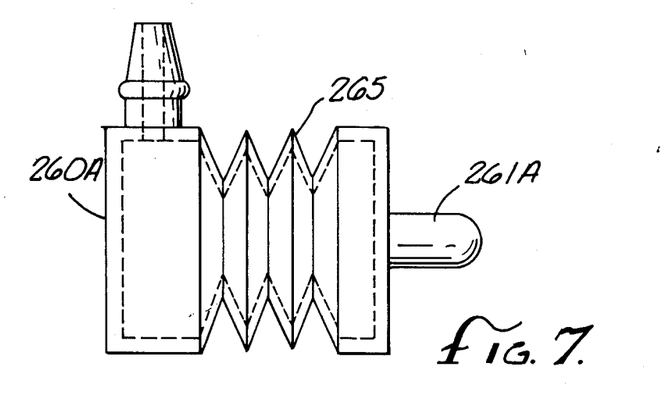
FIG. 7 illustrates the internal portion of a piston/cylinder actuator shown in FIG. 5.

FIG. 7 illustrates the preferred embodiment of a pinch valve acutator 260A utilized in accordance with the present invention. Actuator 260A utilizes an accordian type "baloon" 265 which expands in one direction when the pressure of the fluid therein increases. Portion 265 is molded of a flexible material compatible with the expected service. Piston 261A would function in the manner described for piston 261.

Figure 8:
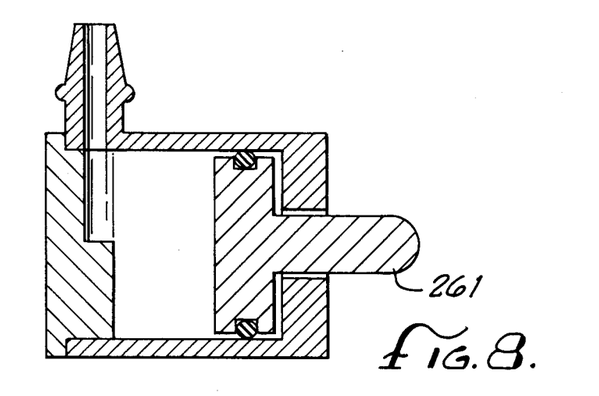
FIG. 8 illustrates a preferred embodiment of the pinch-valve actuator.

FIG. 8 is an expanded view of the internal portion of another version of a piston/cylinder actuator. Piston 261 is dimensioned to provide approximately one pound of pinching force for a line pressure of forty pounds per square inch. The maximum stroke of such piston is approximately 2.5 millimeters. As the skilled artisan will readily appreciate, by activating the pistons 241, 261 and 281 of piston/cylinder actuators 240, 260 and 280 by fluid pressure, efficiency in preventing the flow of fluids in tubing 214, 216 and 218 is maintained without the severe problems found in the prior art, and especially the excess heat generated in the sensor area due to the use of electrically activated valves.

Hybrid circuit 220 is also illustrated in FIG. 5. Circuit 220 contains all the electronics required for amplifying, converting the signals to digital form, as well as multiplexing the signals to simplify the signal transmissions to the balance of the instrumentation. Circuit 220 also contains sockets 224A, 224B, 224C, 224D and 224E for receiving connectors 4A, 4B, 4C, 4D and 4E of the sensors located in housing 10, as well as connector 222 to bring all the sensor signals to the exterior portion of housing assembly 200.

Housing assembly 200 is preferably fabricated of a material suitable for injection molding such as styrene or materials of the like. Most preferably, such material is transparent such that visual observation of the internal housing components is possible. However, housing 220 can be cast in aluminum or any of the variety of metals used to cast complex forms. The area surrounding both sensor 10 and amplifier 220 must be electrostatically shielded to avoid unwanted noise pickup.

Figure 9:
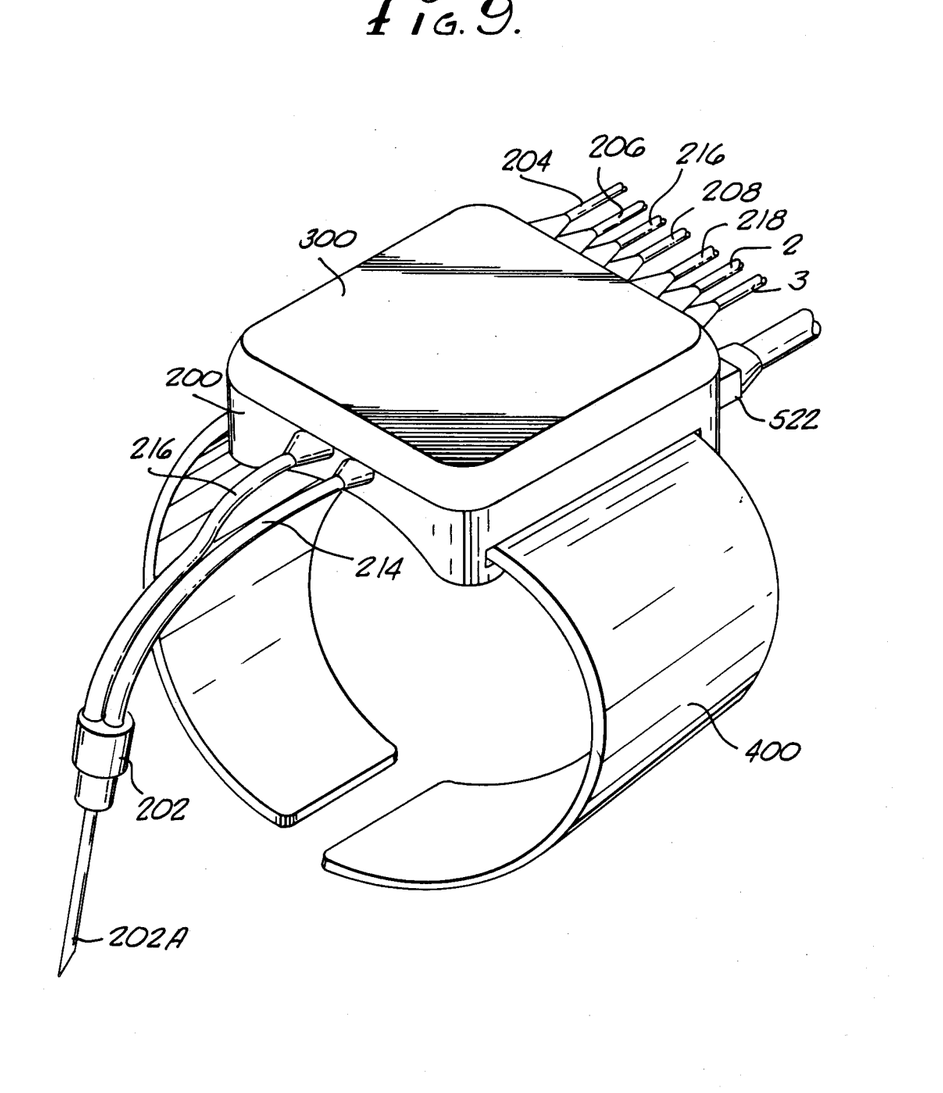
FIG. 9 illustrates the preferred embodiment of the present invention.

The preferred embodiment of the present invention is depicted in FIG. 9. Cover plate 300 fits over housing 200 and should be transparent so that the flow in the system can be visually inspected at all times. In this respect, tubing 214, 216, 218, 204, 206 and 208 can also be transparent. Strap 400 allows for securing the housing to an appendage of the patient, most preferably the wrist, and is preferably made of VELCRO. Fluid lines 214, 216, 218, 204, 206 and 208 and waste line 2 and reference solution line 3 of housing 10 are connected to a pump mechanism (not shown). Connected to such pump would be a source of heparin and baseline solution, as well as a solution for operating piston/cylinder actuators 240, 260 and 280. Additionally, a receptacle for waste material would also be located within proximity to the pump mechanism. Electric connector 522 can be fiberoptic cables connected to output connector 222.

Alternatively, optical coupling can be utilized in accordance with the objectives of the present invention to transmit signals from sensors 101A-D to the computer control console (FIG. 8) by use of fiberoptic cable (not shown). Such conversion of the signal from sensors 101A-D to optical signals can take place within housing 10, and the data can then be transmitted multiplexed to said console.

Figure 10:
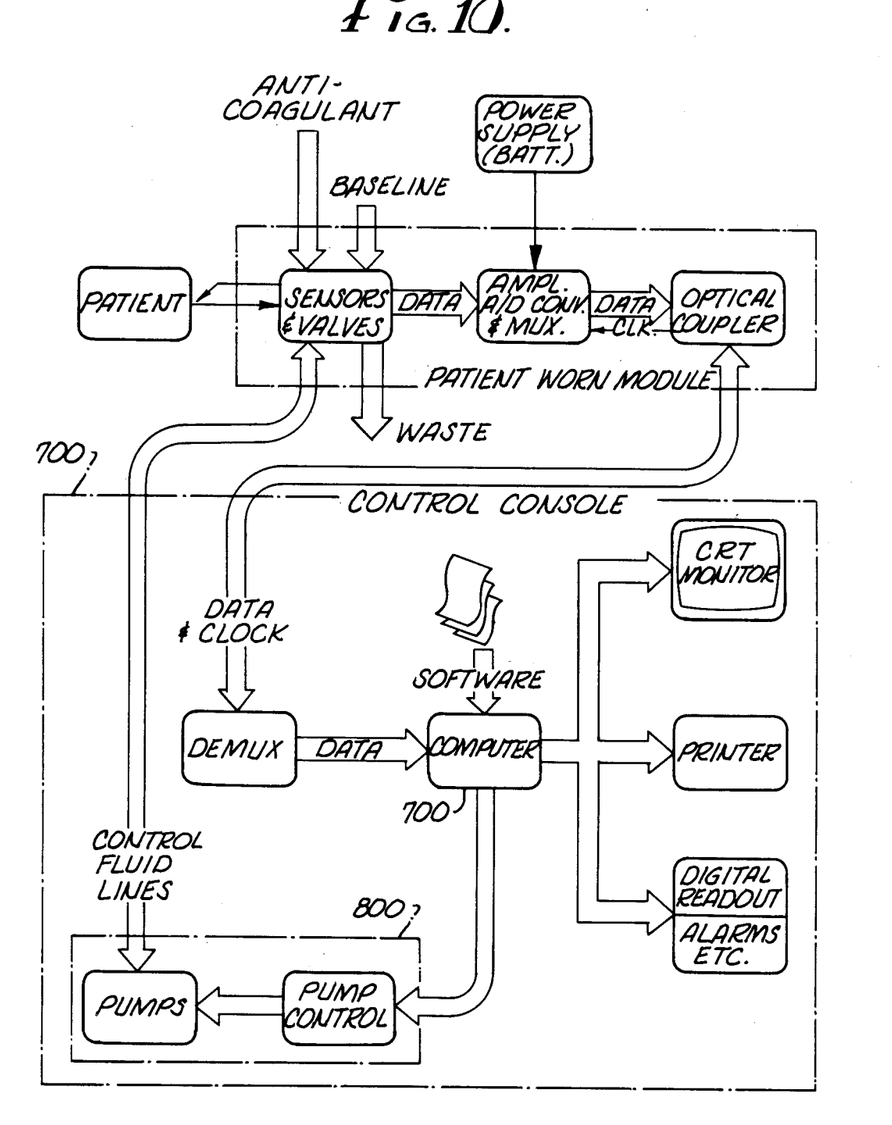
FIG. 10 is a block diagram of the claimed continuous monitoring blood analysis system.

FIG. 10 is a schematic diagram of the present invention, and the skilled artisan will readily understand the functional operation of the measuring instrumentation to which the claimed invention is connected to. In accordance with the present invention, computer 700 is programmed to analyze the data derived from the sensors, and to synchronize the operation of the fluid pumps located within pump housing 800. For example, the flow of heparin will necessarily need to be adjusted during the course of monitoring, as predicated upon the data generated and analyzed by computer 700. In response to specific requirements concerning the need for anti-coagulent, the computer will accordingly command a pump within pump housing 800 to increase/decrease fluid pressure in tube 206; such increase in pressure activates piston 261, which in turn pinches-off or releases the flow of heparin in line 216.

Similarly, computer 700 is programmed to provided for a synchronized flow of analyte through tube 214 and baseline solution through tube 218. Thus, a pump connected to tube 208 will be activated such that an increase in fluid pressure activates piston 281 to prevent the flow of baseline solution in tube 218; at the same time, the pump connected to tube 204 remains at zero or slightly negative pressure such that there is a neutral level of pressure in line 204, whereby piston 241 does not pinch off tube 214. During the next cycle, the above procedure is reversed.

In accordance with the objective of providing continued and reliable data regarding the ionic level of the patient's blood, the present system also provides for connecting a monitor, printer, and alarm indicators to the computer. Thus, if certain preprogrammed ionic concentrations are exceeded during any period of monitoring, an alarm can be activated, thus calling the attention of those responsible for the care of the patient.

While the invention has been described and illustrated with respect to specific embodiments, it is to be understood that modifications and equivalents thereof may be apparent to those skilled in the art and are intended to be within the scope of the invention.

I claim

1. A continuous on-line blood monitoring system for measuring ionic concentrations comprising:
   at least one ion concentration sensor device;
   a first feed line for receiving analyte connected to said sensor device;
   an analyte pinch/cylinder valve actuator operatively connected to said analyte feed line;
   a second feed line for receiving a solution to generate an ionic baseline connected to said sensor device;
   an ionic baseline pinch/cylinder valve actuator operatively connected to said second feed line;
   pumping means for activating and deactivating said analyte pinch/cylinder valve actuator and said ionic baseline pinch/cylinder valve actuator, said pumping means operatively connected to said analyte pinch/cylinder valve actuator and said baseline pinch/cylinder valve actuator;
   means for alternating the operation of said analyte pinch/cylinder valve actuator and said baseline pinch/cylinder valve actuator operatively connected to said pumping means; and
   means for amplifying and sending signals generated by the ionic concentration of said analyte operatively connected to said sensor device.

2. The system of claim 1 wherein said sensor device is a ChemFET.

3. The system of claim 1 wherein said sensor device comprises a sensor plate having on one side thereof at least one sensor electrode having an active area covered with an ion selective membrane and connected to an extended area, said extended area in turn connected to a sensor terminal, and a reference electrode on the side opposite said sensor plate.

4. The system of claim 3 wherein said plate is of a glasslike material of low porosity, inert to both said analyte and a reference solutions.

5. The system of claim 4 wherein said sensor plate is quartz.

6. The system of claim 3 wherein said extended area is overlaid with a coating of silver/palladium.

7. The system of claim 3 wherein said active area is approximately two square millimeters.

8. The system of claim 3 wherein said selective membrane is selective to a specific ion.

9. The system of claim 3 wherein said reference electrode has in the central portion thereof an orifice having a diameter of between approximately 500 and 2,000 microns, preferably 1,000 microns.

10. The system of claim 9 wherein said reference electrode is of a noble metals.

11. The system of claim 1 wherein said means for amplifying and sending signals generated by the ionic concentration of said analyte is a fiberoptic cable.

* * * * *